(12) United States Patent
Chavan et al.

(10) Patent No.: US 8,696,564 B2
(45) Date of Patent: Apr. 15, 2014

(54) IMPLANTABLE SENSOR WITH BIOCOMPATIBLE COATING FOR CONTROLLING OR INHIBITING TISSUE GROWTH

(75) Inventors: Abhi Chavan, Maple Grove, MN (US); Jeffrey Ross, Roseville, MN (US); Cynthia Morrissey, St. Paul, MN (US); Scott Mazar, Woodbury, MN (US); Donald Palme, Princeton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 2732 days.

(21) Appl. No.: 10/888,340

(22) Filed: Jul. 9, 2004

(65) Prior Publication Data

US 2006/0008500 A1 Jan. 12, 2006

(51) Int. Cl.
A61B 5/04 (2006.01)

(52) U.S. Cl.
USPC .......................................... 600/300; 600/310

(58) Field of Classification Search
USPC .................................. 424/423; 600/300, 310
See application file for complete search history.

(56) References Cited

U.S. PATENT DOCUMENTS

| | | | |
|---|---|---|---|
| 5,067,491 A | 11/1991 | Taylor, II et al. |
| 5,683,443 A | 11/1997 | Munshi et al. |
| 5,861,023 A | 1/1999 | Vachon |
| 5,906,824 A | 5/1999 | Suzuki et al. |
| 6,007,876 A | 12/1999 | Niino |
| 6,121,027 A | 9/2000 | Clapper et al. |
| 6,342,591 B1 | 1/2002 | Zamora et al. |
| 6,442,413 B1 | 8/2002 | Silver |
| 6,506,437 B1 | 1/2003 | Harish et al. |
| 6,514,734 B1 | 2/2003 | Clapper et al. |
| 6,544,582 B1 | 4/2003 | Yoe |
| 6,555,157 B1 | 4/2003 | Hossainy |
| 6,616,765 B1 | 9/2003 | Wu et al. |
| 6,673,105 B1 | 1/2004 | Chen |
| 6,673,385 B1 | 1/2004 | Ding et al. |
| 6,712,845 B2 | 3/2004 | Hossainy |
| 6,713,119 B2 | 3/2004 | Hossainy et al. |
| 6,716,444 B1 | 4/2004 | Castro et al. |
| 6,743,462 B1 | 6/2004 | Pacetti |
| 2001/0007082 A1 | 7/2001 | Dusbabek et al. |
| 2002/0124855 A1 | 9/2002 | Chachques |
| 2003/0077452 A1 | 4/2003 | Guire et al. |
| 2003/0099682 A1 | 5/2003 | Moussy et al. |
| 2003/0199837 A1 | 10/2003 | Vachon |
| 2003/0208279 A1 | 11/2003 | Atala |
| 2003/0229393 A1 | 12/2003 | Kutryk et al. |
| 2004/0009589 A1 | 1/2004 | Levenberg et al. |
| 2004/0039441 A1 | 2/2004 | Rowland et al. |
| 2004/0052859 A1 | 3/2004 | Wu et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy |
| 2004/0073284 A1 | 4/2004 | Bates et al. |
| 2004/0073298 A1 | 4/2004 | Hossainy |
| 2004/0078073 A1 | 4/2004 | Bonutti |
| 2004/0086542 A1 | 5/2004 | Hossainy et al. |
| 2004/0102758 A1 | 5/2004 | Davila et al. |
| 2004/0106987 A1 | 6/2004 | Palasis et al. |
| 2004/0116999 A1 | 6/2004 | Ledergerber |
| 2005/0186245 A1* | 8/2005 | Hunter et al. ................. 424/423 |

FOREIGN PATENT DOCUMENTS

| | | |
|---|---|---|
| CA | 2281608 A1 | 8/1998 |
| JP | 09299474 A | 11/1997 |
| JP | 11209493 A | 8/1999 |
| JP | 2001512344 A | 8/2001 |
| JP | 2003532434 A | 11/2003 |
| JP | 2004512062 A | 4/2004 |
| WO | WO-9836782 A2 | 8/1998 |
| WO | WO-9908717 A2 | 2/1999 |
| WO | WO-0206407 A2 | 1/2002 |
| WO | WO-0209647 A2 | 2/2002 |
| WO | WO-03007786 A2 | 1/2003 |
| WO | WO-03055611 A1 | 7/2003 |
| WO | WO-03072157 A1 | 9/2003 |
| WO | WO-03091701 A2 | 11/2003 |
| WO | WO-2004014451 A1 | 2/2004 |
| WO | WO-2006017169 A2 | 2/2006 |
| WO | WO-2006017169 A3 | 2/2006 |

OTHER PUBLICATIONS

"Japanese Application Serial No. 2007-520529, Office Action mailed Aug. 1, 2011", With English Translation, 11 pgs.
"Japanese Application Serial No. 2007520529, Response filed Feb. 1, 2012 to Office Action mailed Aug. 1, 2011", 15 pgs.
"International Search Report and Written Opinion for Application No. PCT/US2005/024250, date mailed Feb. 28, 2006", 21 Pages.
"Invitation to Pay Additional Fees for Application PCT/US2005/024250, mailed Nov. 22, 2005", 7 pgs.
"Japanese Application Serial No. 2007-520529, Office Action mailed Jul. 2, 2012", (English Translation), 6 pgs.

* cited by examiner

*Primary Examiner* — Ruth Davis
(74) *Attorney, Agent, or Firm* — Schwegman Lundberg & Woessner, P.A.

(57) ABSTRACT

All or a portion of a surface of an implantable sensor is covered with a biocompatible coating formed at least partially of a biomaterial matrix having properties that promote a substantially even growth of tissue cells over the surface of the coating. Additional materials, such as growth factors, agents that recruit endogenous stem cells, and cell adhesion motif arginine, glycine, aspartic acid may be included in the coating. Autologous cells may be added to the coating prior to implantation. The sensor surface may also be textured, by etching or abrading, in order to promote even tissue growth. Alternatively, the sensor surface may be covered with a coating having properties that inhibit the growth of tissue. These coatings may include a biomaterial, a biomaterial matrix having a drug, such as a sirolimus or a steroid, an active component, or a self assembled monolayer.

27 Claims, 2 Drawing Sheets

IMPLANTABLE SENSOR WITH BIOCOMPATIBLE COATING FOR CONTROLLING OR INHIBITING TISSUE GROWTH

BACKGROUND OF THE INVENTION

1. Field of the Invention

The invention relates generally to implantable medical devices and, more particularly, to implantable sensors having a biocompatible coating that controls the growth of tissue, or inhibits the growth of tissue, over and around the sensor.

2. Description of Related Art

Human implantable sensors may be used to gather important information about the body's internal environment on a regular basis. Pressure inside an artery, fluid flow inside an artery, body temperature, posture sensing and monitoring of chemical changes are among the different types of information that could be gathered by an implantable sensor.

A problem exists in that any sensor that is implanted into living tissue is subject to tissue growth over and around it. Some tissue growth may be desired in order to embed the sensor and make it a more integral part of the body. However, the sensor's calibration and sensitivity can be adversely effected by different factors of this tissue growth including, but not limited to, the type of tissue that grows over the sensor, the thickness, and the evenness of the tissue growth. For example, in the case of a pressure sensor, the sensitivity of the sensor is affected by the thickness of the tissue while sensor drift is affected by the tension exerted on the sensor by the tissue. This tension, in turn, leads to additional pressure bias that affects the accuracy of the pressure measurements provided by the sensor.

Those skilled in the art have recognized a need for providing a more consistent and predictable growth process in relation to implanted sensors to thereby mitigate the problem of unpredictable tissue growth and its impact on the sensitivity and calibration of sensors. The need for inhibiting tissue growth to further mitigate the foregoing problems has also been recognized. The invention fulfills these needs and others.

SUMMARY OF THE INVENTION

Briefly, and in general terms, the invention is directed to implantable sensors having a biocompatible coating that either controls the growth of tissue, or inhibits the growth of tissue, over and around the sensor. As used herein, "inhibit" means to substantially prevent the growth or formation of tissue. "Control" means to promote the growth or formation of a substantially even layer of tissue.

In one aspect, all or a portion of a sensor surface is covered with a biocompatible coating formed at least partially of a biomaterial matrix having properties that promote a substantially even growth of tissue cells over the surface of the coating. Additional materials, such as growth factors, agents that recruit endogenous stem cells and cell adhesion motif arginine, glycine, aspartic acid may be included in the coating. Also, autologous cells may be added to the coating prior to implantation.

In another aspect, all or a portion of a sensor surface is textured in order to promote even tissue growth over the surface. The texture may be provided by etching or abrading the surface of the interface.

In other aspects, all or a portion of a sensor surface is covered with a coating having properties that inhibit the growth of tissue. These coatings may include a biomaterial, such as polytetraflouroethylene (PTFE) and polyethylene glycol (PEG) or a biomaterial matrix having an active component that imparts growth-inhibiting properties to the coating.

These and other aspects and advantages of the invention will become apparent from the following detailed description and the accompanying drawings which illustrate by way of example the features of the invention.

DETAILED DESCRIPTION OF THE PREFERRED EMBODIMENTS

The invention is directed to implantable sensors which are coated with a biocompatible coating that either controls or inhibits the growth of tissue over and around the sensor. The sensor may be, for example, anyone of a pressure sensor, posture sensor, chemical sensor, temperature sensor or flow sensor that is introduced temporarily or permanently into a mammal for the prophylaxis or therapy of a medical condition and that is designed to monitor physiological activity within the body. These sensors may be introduced subcutaneously, percutaneously or surgically to rest within an organ, tissue or lumen of an organ, such as arteries, veins, ventricles or atrium of the heart.

Figure 1:
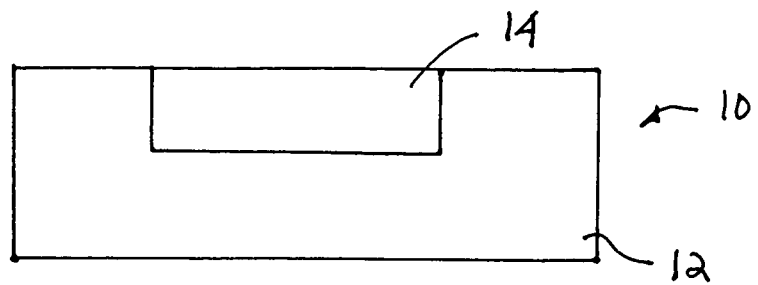
FIG. 1 is a cross section of a sensor including a sensor body and a sensor interface.

With reference to FIG. 1, an exemplary sensor 10 includes a sensor body 12 and a sensor interface 14. The sensor interface 14 is that portion of the sensor 10 that provides the interface between the actual sensing elements (not shown) within the sensor and that portion or element, e.g., blood, vascular tissue, atrial wall, etc., of the body from which the activity being monitored propagates. For example, with respect to a pressure sensor, the sensor interface may include a pressure diaphragm. The sensor interface 14 shown in FIG. 1 is flush with a surface of the sensor body 12. In other sensor configurations, the sensor interface 14 may protrude or project from the surface of the sensor body 12 or may be recessed within the sensor body. The sensor body 12 and/or sensor interface 14 may be made of a biocompatible metal, such as stainless steel, Nitinol, gold, tantalum, titanium, platinum or platinum iridium, or other biocompatible metals and/or alloys such as carbon or carbon fiber. Alternatively, the sensor body 12 and/or sensor interface 14 may be made of a biocompatible plastic or polymer.

The sensor 10 may be included as part of an implanted device, such as the lead of a cardiac rhythm management device, in which case the data gathered by the sensor is transferred to the device through a hardwire electrical connection. The sensor 10 may be configured as a wireless device, in which case the sensor interface 14 may include a transmission device for transmitting the data gathered by the sensor to a receiver remote from the sensor. For example, the sensor interface 14 may be formed of an optically compatible material that allows for certain wavelength of intra-red light to pass efficiently. In this configuration, the biocompatible coating not only serves to maintain sensor calibration and sensitivity, it also protects against interference that uneven tissue growth may impart on data transmission between transmitter and receiver. A wireless sensor may, for example, be mounted to a stent to facilitate implantation.

While the sensor 10 shown in FIG. 1 includes only one sensor interface 14, a sensor may have more than one such interface. For example, a wireless sensor may have one sensor interface 14 for its sensing functions and a second, separate sensor interface for its data transmission functions. The biocompatible coating 16 covers at least one of these interfaces 14 and preferably, both of the interfaces.

Figure 2A:
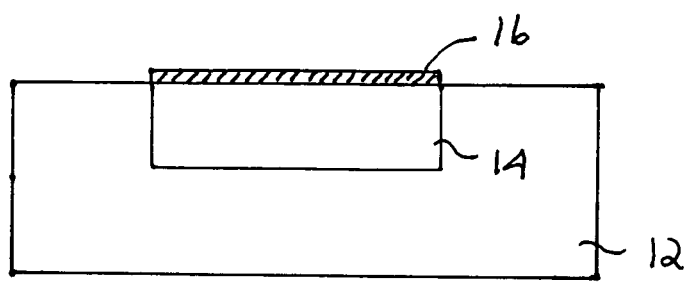
FIG. 2a is a cross section of the sensor of FIG. 1 including a biocompatible coating over a surface of the sensor interface.
Figure 2B:
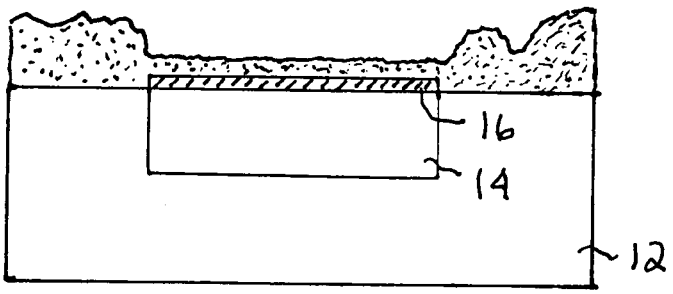
FIG. 2b is a cross section of the coated sensor of FIG. 2a depicting substantially even tissue growth over the coated surface of the sensor interface and uneven tissue growth over the uncoated surface of the sensor body.
Figure 2C:
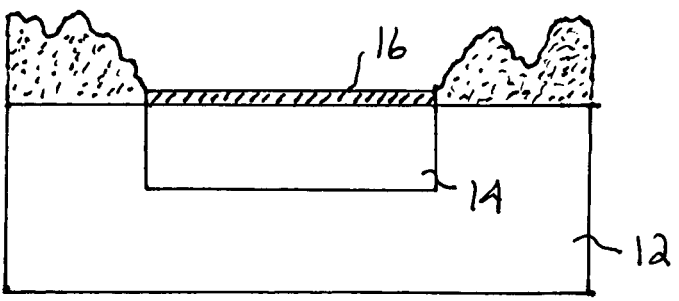
FIG. 2c is a cross section of the coated sensor of FIG. 2a depicting substantially no tissue growth over the coated surface of the sensor interface and uneven tissue growth over the uncoated surface of the sensor body.
Figure 3A:
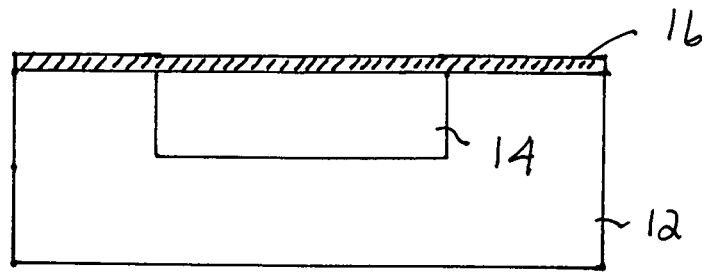
FIG. 3a is a cross section of the sensor of FIG. 1 including a biocompatible coating over a surface of the sensor interface and a surface of the sensor body.
Figure 3B:
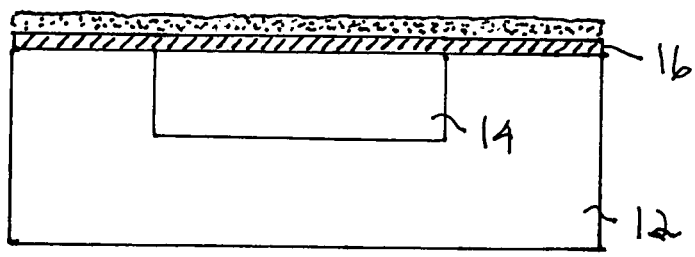
FIG. 3b is a cross section of the coated sensor of FIG. 3a depicting substantially even tissue growth over the coated surface of the sensor interface and the coated surface of the sensor body.
Figure 3C:
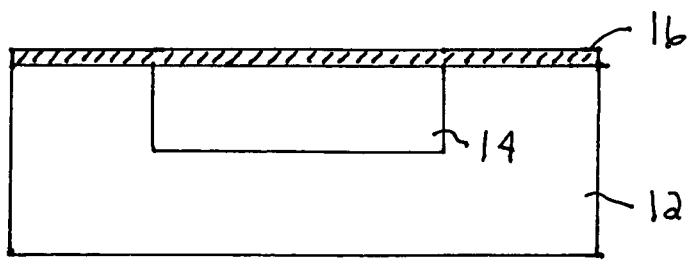
FIG. 3c is a cross section of the coated sensor of FIG. 3a depicting substantially no tissue growth over the coated surface of the sensor interface and the coated surface of the sensor body.

With reference to FIG. 2a, the sensor 10 may be configured such that a layer 16 of the biocompatible coating covers only a surface of the sensor interface 14 portion of the sensor 10. Alternatively, as shown in FIG. 3a, the layer 16 may cover the entire surface of the sensor 10 including the sensor interface 14. In other configurations (not shown), the entire surface of the sensor body or only select portions may be covered with the coating. As explained further below, in all configurations, the composition of the coating is such that it either promotes an even layer of cell growth over the coated surfaces of the sensor (as shown in FIGS. 2b and 3b) or it inhibits cell growth over the coated surfaces of the sensor (as shown in FIGS. 2c and 3c). Thus, after implantation of the sensor, the sensitivity and calibration of the sensor will, in the case of even tissue growth, change in a way that is more predictable or, in the case of substantially no tissue growth, not experience a significant change. The inhibition of tissue growth and/or the promotion of a more even tissue growth of a particular type helps to ensure that the sensor's sensitivity and calibration changes remain within a desired range and facilitates sensor recalibration after tissue growth.

In one embodiment, the biocompatible coating consists of a biomaterial matrix favorable to tissue growth allowing for formation of a substantially even neointimal layer of tissue over the sensor. The biomaterial matrix comprises a polymer, oligomer or co-polymer for coating the sensor from various types and sources, including, natural or synthetic polymers, which are at least biocompatible. The polymers may also be biodegradable and/or bioabsorbable. For example, a natural polymer such as an extracellular matrix (ECM) material may be used, including, for example, intestine submucosa (SIS) and urinary bladder matrix (UBM) substances. Such ECMs are composed of three major classes of biomolecules including structured proteins, e.g., collagen and elastin, specialized proteins, e.g., fibrillin, fibronectin and laminin and proteoglycans. Proteoglycans are composed of a protein core to which is attached long chains of repeating disaccharide units termed of glycosaminoglycans (GAGs) forming extremely complex high molecular weight components of the ECM. Independent of their inclusion in the ECMs, both proteoglycans and proteins, including collagen, fibrin, elastin, fibrillin, fibronectin, and laminin, may themselves be used as the polymer. Another example of a natural polymer which may be used as a coating is phosphytidyl choline.

Synthetic polymers may be selected from polyhydroxyvalerate, poly(L)lactic acid, polycaprolactone, polylactide-co-glycolide, polyhydroxybutyrate, polyhydroxybutyrate-co-valerate, polydioxanone, polyorthoesters, polyanhydrides, polyacetic or polyglycolic acid and derivatives thereof, poly (D,L)lactic acid, polyglycolic acid-co-trimethylene carbonate, polysebacic acid, polylactic-co-sebacic acid, polyglycolic-co-sebacid acid, polyphosphoesters, polyphosphoester urethanes, polyamino acids, such as polylysine, lactic/glycolic acid copolymers, and ion exchange resins such as sulfonated polytetrafluoroethylene, or combinations thereof; cyanoacrylates, polytrimethylene carbonate, polyiminocarbonate, copolyether-esters (e.g., PEO/PLA), polyalkylene oxalates and polyphosphazenes. Polymers with a relatively low chronic tissue response such as polyurethanes, silicones, and polyesters could be used.

Other polymers could also be used if they can be dissolved and cured or polymerized on the sensor such as polyolefin, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; rayon and rayon-triacetate.

The polymer coating may be applied to the sensor is any one of several ways known in the art including those disclosed in the following U.S. patents, the disclosures of which are hereby incorporated by reference: U.S. Pat. No. 6,713,119, titled "Biocompatible Coating for a Prosthesis and a Method of Forming the Same," U.S. Pat. No. 6,673,385, titled "Methods for Polymeric Coating Stents," U.S. Pat. No. 6,616,765, titled "Apparatus and Method for Depositing a Coating onto a Surface of a Prosthesis," U.S. Pat. No. 6,555,157, titled "Method for Coating an Implantable Device and System for Performing the Method," U.S. Pat. No. 6,544,582, titled "Method and Apparatus for Coating an Implantable Device" and U.S. Pat. No. 6,506,437, titled "Methods of Coating an Implantable Device Having Depots Formed in a Surface Thereof."

In another embodiment, the biocompatible coating includes a biomaterial matrix having an added growth factor, agent, cytokine or the like, which stimulates local cell growth to promote a substantially even tissue growth. The coating is preferably formed to provide a sustained release of the agent. The biomaterial matrix may be either a natural or synthetic polymer like those previously listed. The added growth factor may include one or more of vascular endothelial cell growth factor (VEGF) and isoforms, basic fibroblast growth factor (bFGF), platelet-induced growth factor (PDGF), transforming growth factor beta (TGF.b), acidic fibroblast growth factor (aFGF), osteonectin, angiopoietin 1, angiopoietin 2, insulin-like growth factor (IGF), platelet-derived growth factor AA (PDGF-AA), platelet-derived growth factor BB (PDGF-BB), platelet-derived growth factor AB (PDGF-AB), granulocyte-macrophage colony-stimulating factor (GM-CSF), and the like, or functional fragments thereof.

In another embodiment, the biocompatible coating includes a biomaterial matrix having an added agent, cytokine or the like, which recruits endogenous stem cells to promote a substantially even tissue growth. The coating is preferably formed to provide a sustained release of the agent. The biomaterial matrix may be either a natural or synthetic polymer like those previously listed. The added agent may include one or more of granulocyte colony-stimulating factor (G-CSF), stem cell factor (SCF-1), stromal-derived factor (SDF-1), insulin-like growth factor (IGH) or hepatocyte growth factor (HGF).

In another embodiment, the biocompatible coating includes a biomaterial matrix having attached thereto a cell adhesion motif arginine, glycine, aspartic acid (RGD), which is a ligand for integrin cell adhesion receptors. RGD recruits the adhesion of cells and thus forms a type of neointimal layer of endothelia cells to thereby promote a substantially even tissue growth. The biomaterial matrix may be either a natural or synthetic polymer like those previously listed.

In each of the preceding three embodiments, the biocompatible coating, i.e., biomaterial matrix plus added growth factor, agent and/or RGD, may be formed and applied to the sensor is any one of several ways known in the art including those disclosed in the previously cited U.S. patents and the following U.S. patents, the disclosures of which are also hereby incorporated by reference: U.S. Pat. No. 6,743,462, titled "Apparatus and Method for Coating Implantable Devices," U.S. Pat. No. 6,716,444, titled "Barriers for Polymer-Coated Implantable Medical Devices and Method for Making the Same" and U.S. Pat. No. 6,712,845, titled "Coating for a Stent and a Method of Forming the Same."

In another embodiment, the biocompatible coating is formed to provide a sustained release of an active component that inhibits tissue growth. The coating is formed of a biomaterial matrix, like those previously listed, and an active component. The active component may include, for example, a sirolimus or a steroid. The coating may be formed and applied to the sensor in any one of the ways described in the previously cited U.S. patents.

Alternatively, the active component may include an anti-thrombotic substance and an anti-inflammatory substance. Possible anti-thrombotic substances include heparin, sodium heparin, low molecular weight heparin, hirudin, argatroban, forskolin, vapiprost, prostacyclin and prostacyclin analogs, D-phe-pro-arg-chloromethylketone, dipyridamole, glycoprotein IIb/IIIa platelet membrane receptor antibody, and recombinant hirudin. Possible anti-inflamatory substance includes aspirin, diclofenac, etodolac, ibuprofen, ketoprofen, ketorólac, nabumetone, naproxen, oxaprozin, clobetasol, diflucortolone, flucinolone, halcinolonide, halobetasol, dexamethasone, betamethasone, corticol, cortisone, prednisone, and prednisolone.

In another configuration, instead of the anti-thrombotic substance of the active component being released, the sensor is coated with an anti-thrombogenic material which is not substantially released from the surface. Such anti-thrombogenic coatings can be made from either an active thrombin inhibitor, typically heparin, a heparin derivative, or a heparin analog, or can be made from a passively thromboresistant material, such as a hydro-gel, or any combination of active and passive thromboresistant material. Examples of useful hydro-gels include poly-ethylene oxide, albumin, hydrophilic poly-(meth)acrylates, and hydrophilic poly-urethanes. In another embodiment, an anti-thrombotic substance may also be releasably contained with the anti-inflammatory substance in the anti-thrombogenic coating. Details of these active components are disclosed in U.S. Patent Application Publication No. 20010007082, titled "Device and Active Component for Inhibiting Formation of Thrombus-Inflammatory Cell Matrix," which is hereby incorporated by reference.

In another embodiment, the biocompatible coating is a biomaterial having properties that substantially inhibit growth of tissue cells over its surface. The biomaterial may be polytetraflouroethylene (PTFE) or polyethylene glycol (PEG). In another configuration, the biomaterial is formed of an anti-thrombogenic material, such as those described above. The material may be applied to the sensor in any one of several ways known in the art.

In another embodiment, substantially even tissue cell growth is promoted by texturing portions of the sensor. As used herein, a "textured" surface includes a surface that is roughened, unsmooth or uneven. For example, metallic portions of the sensor may be textured by etching or abrading the surface of the metal. Such texturing is intended to promote cell adhesion to the surface of the metal which will lead to the formation of a neointimal layer of endothelial cells and ECM which then inhibits the formation of thrombosis or other potential fibrotic responses.

In another embodiment, the biocompatible coating includes a biomaterial matrix that is applied during the manufacturing of the sensor (using known methods or those method described in the U.S. patents previously incorporated by reference) and an additive including autologous cells that are added to the matrix after the manufacturing process and at a pre-defined time prior to actual implantation of the sensor in the body. The autologous cells may be added to the biomaterial matrix by any standard method.

In one such embodiment, the additive includes disassociated autologous cells which may be harvested from the patient's mesenchymal stem cells (MSC), endothelial progenitor cells (EPC), smooth muscle cells (SMC), endothelial cells, hematopoietic stem cells, for instance, cells from cord blood and isolated $CD34^+$ cells, multipotent adult progenitor cells, side population stem cells, adult stem cells and embryonic stem cells or differentiated cells derived from any of, but not limited to, the stem cells listed above. The biomaterial matrix with autologous cells is preferably cultured in vitro prior to implantation in the patient. The particular autologous cells added to the matrix may be selected based on the implantation cite. For example, EPC cells would most likely be used for intra artery implants while SMC cells would be used for intra muscle implants.

Possible biomaterial matrixes for use in this embodiment include the polymers previously listed. Other useful polymers include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials.

In another embodiment, the biocompatible coating includes a self-assembled monolayer (SAM) coating, such as pre-formed carboxylic acid alkanethiolate. This coating prevents cell growth and thus the growth of tissue on the sensor surface. In this embodiment, the sensor surface includes gold which allows for the attachment of the SAM coating. The gold may be an integral part of the sensor surface or, alternatively, the gold may be included in a layer of metallic material that is applied to the sensor surface prior to the application of the SAM coating.

While the sensors shown in the figures and described have only one type of biocompatible coating, i.e., either growth inhibiting or even-growth promoting, a sensor may be coated with both types of coatings. For example, it may be beneficial to apply the growth inhibiting coating only to the sensor interface and the even-growth promoting coating to the remainder of the sensor.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A sensor comprising:
a sensor having a sensor body, a sensor interface and a data transmission interface, each having a surface; and
a biocompatible coating covering at least the surface of the sensor interface, the coating comprising a biomaterial matrix and an active component, wherein the active component imparts properties to the coating that inhibits the growth of tissue over the sensor interface.

2. The sensor of claim 1 wherein the biomaterial matrix comprises a natural polymer.

3. The sensor of claim 2 wherein the natural polymer comprises extracellular matrix material.

4. The sensor of claim 3 wherein the extracellular matrix material is a material selected from the group consisting of intestine submucosa and urinary bladder matrix.

5. The sensor of claim 2 wherein the natural polymer comprises a protein.

6. The sensor of claim 5 wherein the protein is selected from the group consisting of collagen, fibrin, elastin, fibrillin, fibronectin, and laminin.

7. The sensor of claim 5 wherein the natural polymer comprises proteoglycans.

8. The sensor of claim 5 wherein the natural polymer comprises phosphytidyl choline.

9. The sensor of claim 1 wherein the biomaterial matrix comprises a synthetic polymer.

10. The sensor of claim 9 wherein the synthetic polymer is selected from the group consisting of polyhydroxyvalerate, poly(L)lactic acid, polycaprolactone, polylactide-co-glycolide, polyhydroxybutyrate, polyhydroxybutyrate-co-valerate, polydioxanone, polyorthoesters, polyanhydrides, polyacetic, polyglycolic acid, poly(D,L)lactic acid, polyglycolic acid-co-trimethylene carbonate, polysebacic acid, polylactic-co-sebacic acid, polyglycolic-co-sebacid acid, polyphosphoesters, polyphosphoester urethanes, polyamino acids, ion exchange resins, cyanoacrylates, polytrimethylene carbonate, polyiminocarbonate, copolyether-esters, polyalkylene oxalates and polyphosphazenes.

11. The sensor of claim 9 wherein the synthetic polymer is selected from the group consisting of polyurethanes, silicones and polyesters.

12. The sensor of claim 9 wherein the synthetic polymer is selected from the group consisting of polyolefin, polyisobutylene, ethylene-alphaolefin copolymers, acrylic polymers and copolymers, vinyl halide polymers and copolymers, polyvinyl ethers, polyvinylidene halides, polyacrylonitrile, polyvinyl ketones, polyvinyl aromatics, polyvinyl esters, copolymers of vinyl monomers with each other and olefins, polyamides, alkyd resins, polycarbonates, polyoxymethylenes, polyimides, polyethers, epoxy resins, rayon and rayon-triacetate.

13. The sensor of claim 1 wherein the active component comprises a sirolimus.

14. The sensor of claim 1 wherein the active component comprises a steroid.

15. The sensor of claim 1 wherein the active component comprises at least one anti-thrombotic substance and at least one anti-inflammatory substance.

16. The sensor of claim 15 wherein the anti-thrombotic substance is selected from a group of heparin, sodium heparin, low molecular weight heparin, hirudin, argatroban, forskolin, vapiprost, prostacyclin and prostacyclin analogs, D-phe-pro-arg-chloromethylketone, dipyridamole, glycoprotein IIb/IIIa platelet membrane receptor antibody, and recombinant hirudin; and the anti-inflamatory substance is selected from a group of aspirin, diclofenac, etodolac, ibuprofen, ketoprofen, ketorolac, nabumetone, naproxen, oxaprozin, clobetasol, diflucortolone, flucinolone, halcinolonide, halobetasol, dexamethasone, betamethasone, corticol, cortisone, prednisone, and prednisolone.

17. The sensor of claim 1 wherein the sensor body has a surface and the sensor interface protrudes or projects from the surface of the sensor body.

18. The sensor of claim 1 wherein the sensor interface is recessed within the sensor body.

19. The sensor of claim 1 wherein the sensor interface comprises a transmission device configured to transmit data gathered by the sensor.

20. The sensor of claim 1 wherein the sensor body has a body surface, the sensor interface has an interface surface, and the biocompatible coating covers portions of the body surface and the interface surface.

21. The sensor of claim 1 wherein the interface allows for the transmission of infra-red light.

22. A sensor comprising:
a pressure sensor having a sensor body, a sensor interface and a data transmission interface, each having a surface; and
a biocompatible coating on the surface of the sensor interface comprising biomaterial matrix and an agent that inhibits the growth of tissue over the surface of the sensor interface.

23. The sensor of claim 22 wherein the agent comprises polytetrafluoroethylene or polyethylene glycol.

24. The sensor of claim 22 wherein the agent comprises a steroid or sirolimus.

25. The sensor of claim 22 wherein the sensor interface comprises a pressure diaphragm.

26. A method of monitoring biological activity within a body, said method comprising introducing a sensor in the body in the region to be monitored, wherein the sensor comprises a sensor body, a sensor interface and a data transmission interface, each having a surface, and a biocompatible coating covering at least the surface of the sensor interface, the coating comprising a biomaterial matrix and an active component, wherein the active component imparts properties to the coating that inhibit the growth of tissue over the surface of the coating.

27. A process of manufacturing a sensor comprising a sensor body, a sensor interface and a data transmission interface, each having a surface, for implantation into a body, said process comprising coating at least the surface of the sensor interface with a biocompatible coating comprising a biomaterial matrix and an active component, wherein the active component imparts properties to the coating that inhibit the growth of tissue cells over the surface of the coating.

* * * * *